(12) United States Patent
Asami et al.

(10) Patent No.: US 6,193,712 B1
(45) Date of Patent: Feb. 27, 2001

(54) TREATMENT APPARATUS

(75) Inventors: Norisumi Asami, Saitama; Haruo Sekiguchi, Kanagawa, both of (JP)

(73) Assignee: Yugen Kaisha B.A.S. (JP)

( * ) Notice: Subject to any disclaimer, the term of this patent is extended or adjusted under 35 U.S.C. 154(b) by 0 days.

(21) Appl. No.: 09/359,664

(22) Filed: Jul. 26, 1999

(30) Foreign Application Priority Data

Jul. 30, 1998 (JP) .................................................. 10-247687

(51) Int. Cl.⁷ .................................................. A61B 18/18
(52) U.S. Cl. .................................. 606/13; 604/35; 606/41
(58) Field of Search .................................. 606/41, 45, 27, 606/13–17, 169, 170; 62/5–7, 606–615; 604/35

(56) References Cited

U.S. PATENT DOCUMENTS

| | | | |
|---|---|---|---|
| 3,831,430 | * | 8/1974 | Azinger, Jr. ........................... 73/71 A |
| 4,919,232 | * | 4/1990 | Lofton .................................. 184/6.26 |
| 5,349,778 | * | 9/1994 | Chu ........................................ 43/124 |
| 5,431,650 | * | 7/1995 | Cosmescu ............................... 606/41 |
| 5,836,944 | * | 11/1998 | Cosmescu ............................... 606/41 |
| 6,099,525 | * | 8/2000 | Cosmescu ............................... 606/41 |

FOREIGN PATENT DOCUMENTS

| | | |
|---|---|---|
| 6-307731 | 11/1994 | (JP) . |
| 7-332780 | 12/1995 | (JP) . |
| 9-004937 | 1/1997 | (JP) . |
| 9-159298 | 6/1997 | (JP) . |
| 10-165523 | 6/1998 | (JP) . |

* cited by examiner

Primary Examiner—Linda C. M. Dvorak
Assistant Examiner—Ahmed Farah
(74) Attorney, Agent, or Firm—Nixon & Vanderhye P.C.

(57) ABSTRACT

A medical treatment apparatus generates moving cold and hot gas streams by supplying air having a low dew point (after being compressed, liquefied or dried subsequent to a compression step) to a vortex tube while the air cleanliness level thereof is improved by removal of oily substances and solid particles to negligible levels. The medical treatment apparatus most preferably includes a hand piece for medical treatment, a vortex tube and a retaining assembly which adjustably retains the vortex tube on said hand piece and allows for positional adjustment of the vortex tube relative to a medical treatment area. The retaining assembly includes a first retaining member attached to the vortex tube, and a second retaining member attached to the hand piece, with the first and second retaining members being pivotally connected to each other. The apparatus further may be provided with an oil-free scroll type compressor, an air filter assembly; a heat-less drier; an electromagnetic valve; and a filter which are connected in series in that order to communicate with the vortex tube.

6 Claims, 4 Drawing Sheets

TREATMENT APPARATUS

BACKGROUND OF THE INVENTION

The present invention relates to a treatment apparatus which generates cold and hot winds by supplying an air having a low dew point (after being compressed, liquefied or dried subsequent to a compression step) to a vortex tube while the air cleanliness level is improved, oily substances and solid particles are removed to a negligible extent. While being able to be applied to industrial use such as cooling of IC chips or other works, the apparatus is a cold and hot wind producer which finds other applications in the medical field, for example, a laser beam medical apparatus such as a laser surgical knife.

As examples of the laser beam medical treatment apparatus like a laser surgical knife, there have been proposed a laser medical treatment device which cools the diseased skin under treatment by jetting thereto an atomized mixture fluid of a gas and a liquid while the laser beam irradiattion is being conducted for treatment (Japanese Pat. Appln. Pub. No. 07051287) or a device and method for cooling the skin during the laser beam treatment by means of an electronic (Peltier effect) cooling means (Japanese Pat. Appln. Pub. No. 10-165523). Further, there has been proposed a method in which a cold liquid is sprayed, a cold storage medium such as a polymeric gel water absorbing agent or a chilling agent showing an endothermic reaction is applied directly on the diseased skin. However, the treatment by the laser beam by use of the laser beam surgical knife creates the need for the diseased skin to be locally cooled and for the cooling medium to be dried during the treatment but any of the above mentioned prior art methods will not meet the requirements to control the laser beam treatment. Further, the conventional electronic (Peltier effect) cooling device is so difficult to handle that it is impossible to place the device on the diseased skin. Therefore, the present invention is aimed at producing cold and hot winds by means of a vortex tube, connect such wind producing device to the laser beam means such as the laser surgical knife, the ultrasonic surgical knife, or the massaging device for ease of operation such that any diseased skin portion is cooled by the cold wind from the vortex tube which efficiently produces cool and hot winds while maintaining a high level of air cleanliness acceptable for medical use by reducing oily substances, solid particles or odors. In this connection, said vortex tube is an instrument constructed on the basis of the vortex effect which was discovered by a French physicist by the name of Georges Ranque in the first half of this century and evaluated by Rudolph Hilsch in his thesis in mid 1940s. In general, the tube constructed on the basis of this effect is known "Hilsch Tube". There is a conventional cold wind producing device which is aimed at saving the energy by producing a cool wind by means of such vortex tube after the moisture is removed by a membrane module or the like. (Japanese Pat. Appln. Pub. No. 7-332780). However, such a device tends to be large sized and creates problems in attaching the same to the medical device because the membrane module must be attached onto the vortex tube.

There are printed publications using other examples of Japanese Pat. Appln. Pub. No. 6-307731) which discloses that compressed air is introduced into a vortex tube to produce a low-temperature air and a high temperature air for use of air-conditioning. Another publication is Japanese Pat. Appln. Pub. No. 9-4937 which is directed to the vortex tube per se. There is a further publication which is Japanese Pat. Appln. Pub. No. 9-159298 disclosing a vortex tube for use in a cooling system in general.

However, all of these printed publications fail to disclose that such vortex tube is mounted onto the hand piece for medical treatment in such a manner that the jetted air is locally directed to any diseased portion.

SUMMARY OF THE INVENTION

Therefore, the first object of the present invention is to provide a treatment apparatus which is so compact and easy to operate and handle that it is capable of cooling, warming or drying the diseased portion to be treated;

the second and third objects in addition to the first object are to provide a treatment apparatus which can be locally directed to any diseased skin portion to be treated with the aid of the vortex tube;

the forth object in addition to the first or the second object is to provide a treatment apparatus which is capable of easily providing a fine tuning to the vortex tube mounting positioning and the jetting range such that the vortex tube is accurately directed to any diseased portion to be treated because the mounting position is adjusted by allowing a retaining metal member to move back and forth and to rotate;

the fifth and sixth objects in addition to the first to third objects are to provide a treatment apparatus by which the dew point of the air to be compressed is lowered such that the cold and hot winds are efficiently produced by the vortex tube;

the seventh object in addition to the fifth object is to provide a treatment apparatus the maintenance of which is easy, the air cleanliness of which is improved, in which oily substances are reduced, and in which solid particles are removed; and the eighth object in addition to the first through eighth objects is to provide a treatment apparatus which is mounted onto the laser beam surgical knife, the ultrasonic surgical knife; the massage vibrator or the like such that a hot wind is used for a massaging aid.

In order to realize the above mentioned objects, the present invention provides a treatment apparatus comprising a hand piece for medical treatment; and a vortex tube; and means for adjustably retaining said vortex tube on said hand piece.

DESCRIPTION OF THE EMBODIMENTS

Figure 1:
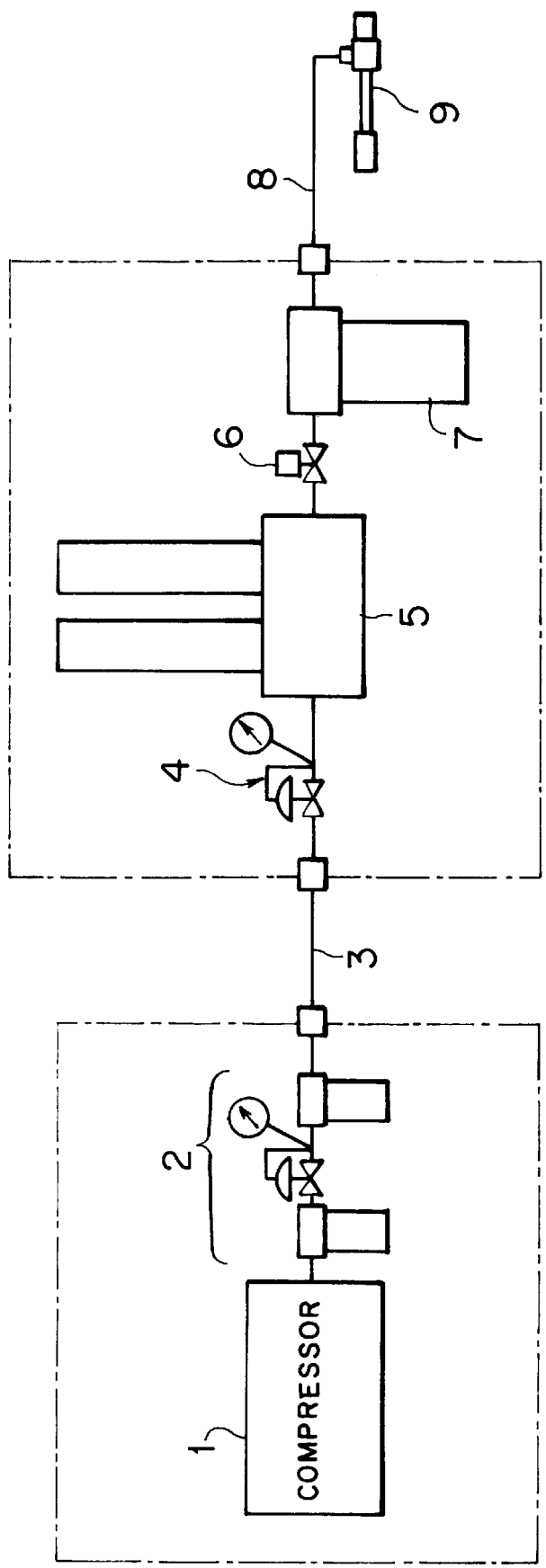
FIG. 1 is a block diagram of one embodiment of the present invention.

Hereinafter, an embodiment of the present invention will be described. FIG. 1 shows a diagram of the cold or hot winds producing device in accordance with the flow of the medium which will hereinafter be explained. The air is compressed by means of compressor 1 to increase the pressure thereof. Said compressor 1 is of an oil-free scroll type. The compressed air thereby is fed to the conduit 3 by way of an air filter assembly 2 with a pressure reducing valve between an air filter and a mist separator. Said compressor 1 and said air filter assembly 2 are installed outdoors while air pressure reducing valve 4 and the other elements thereafter are installed indoors. Further, the compressed air is guided by way of said conduit 3 to air pressure reducing valve 4, to heat-less drier 5, to the electromagnetic valve 6, to filter 7 of high filtering rating, to conduit 8, and, then, to vortex tube 9, where a vortex flow is generated with the compressed air at the vortex flow producing section thereof to produce a high temperature air or a low temperature air. In this embodiment, the heat-less drier 5 uses zeolite as an absorbent but other known absorbent may be used in place thereof. In this way, the compressed air has its moisture removed by heat-less drier 5 to make a dew point thereof lower such that the vortex tube efficiently generates a cold wind and hot winds. For making the dew point of the compressed air even lower, liquefied nitrogen gas having a low dew point may be used as a compressed air. In this connection, said outdoor portion of the device and the indoor portion of the device may be integrated to be installed indoors. One example of said vortex tube 9 is designed as follows; that is, if the inflow air temperature is set at 20 degrees centigrade with the inflow pressure at 0.7 Mpa (normally at 7 Kgf/cm²), maximum working pressure at 0.9 Mpa (normally at 9 Kgf/cm₂), normal working pressure at 0.7 Mpa (normally 7 Kgf/cm₂), the cold wind temperature of 30 degrees centigrade below zero is obtained. The air filter assembly 2 with the air pressure reducing valve between the air filter and the mist separator, electromagnetic valve 6, and filter 7 of high filtering rating are arranged together with vortex tube 9 such that air cleanliness reaches the level at which oily substances are at 0.01 ppm (W/W) or less and the solid particles of 0.025 μm or more are removed. Deodorizing is also done.

Figure 4:
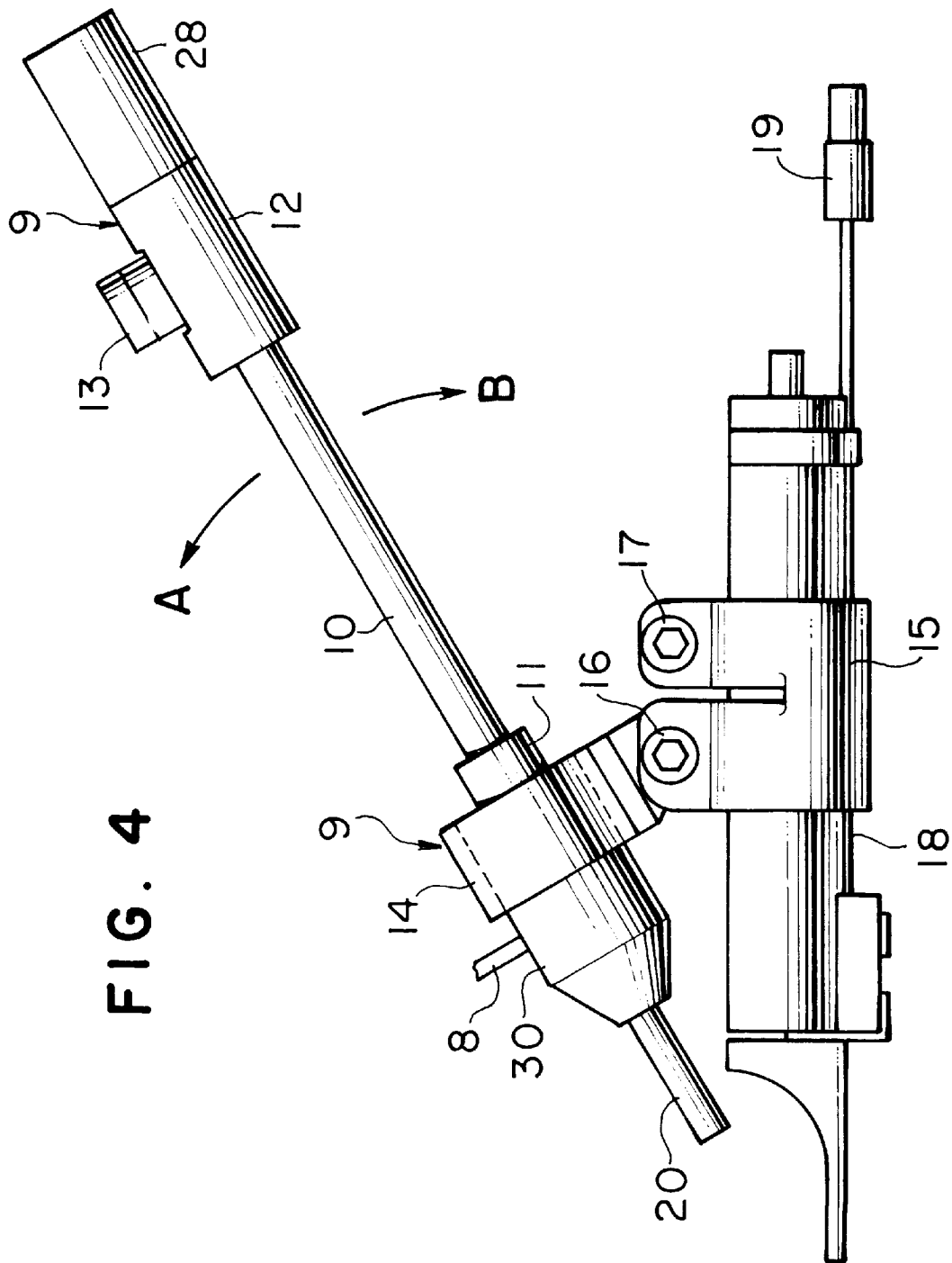
FIG. 4 is a front view of an enlarged portion of the treatment apparatus of the invention.

Further, as shown in FIG. 4, tubular coupling joint 12 is screwed onto the rearward portion of tubular body 10 of vortex tube 9 to provide hot wind exhaust port 28 (in case of a cold wind, an exhaust pipe to the outside may be attached at the rearward end thereof) and regulating valve 13. Further, tubular coupling joint 11 is screwed onto the forward end of tubular body 10. Body 30 having a nozzle (not shown) jetting compressed high pressure air in the direction of a tangent line and a cold wind exhaust port 20 extending in the direction of a tangent line is connected to said tubular coupling joint 11. Further, first and second retaining metal members 14 and 15 are engaged with said body 30 and said laser beam hand piece 18, respectively, with said second retaining member being adapted to move back and forth and rotate axially on the hand piece 18. Said retaining metal members 14 and 15 are tightened by adjust screws 16. Said adjust screws 16 may be replaced with bolts and nuts. The angle at which said vortex tube 9 is mounted onto the hand piece 18 can be adjusted as shown by arrows A and B by tightening and loosening said adjust screw 16. Further, the back and forth movement (jetting distance) and the axial rotation (to change the position of the vortex tube relative to the hand piece) of the retaining metal member 15 are adjusted by tightening and loosening said adjust screws 17 (or bolts and nuts) of the retaining metal member 15 of the hand piece 18. As a result, vortex tube is capable of being directed to any portion of the diseased skin to be treated and the positioning, the movement and the rotation of said vortex tube is easily done and stopped. The numeral 19 denotes a cable for the laser beam device or the like. Although not shown, the cold/high temperature wind generating sections 20 and 28 located at the leading end and the trailing end portions of the vortex tube 9 may be covered by a heat insulating material.

Figure 2:
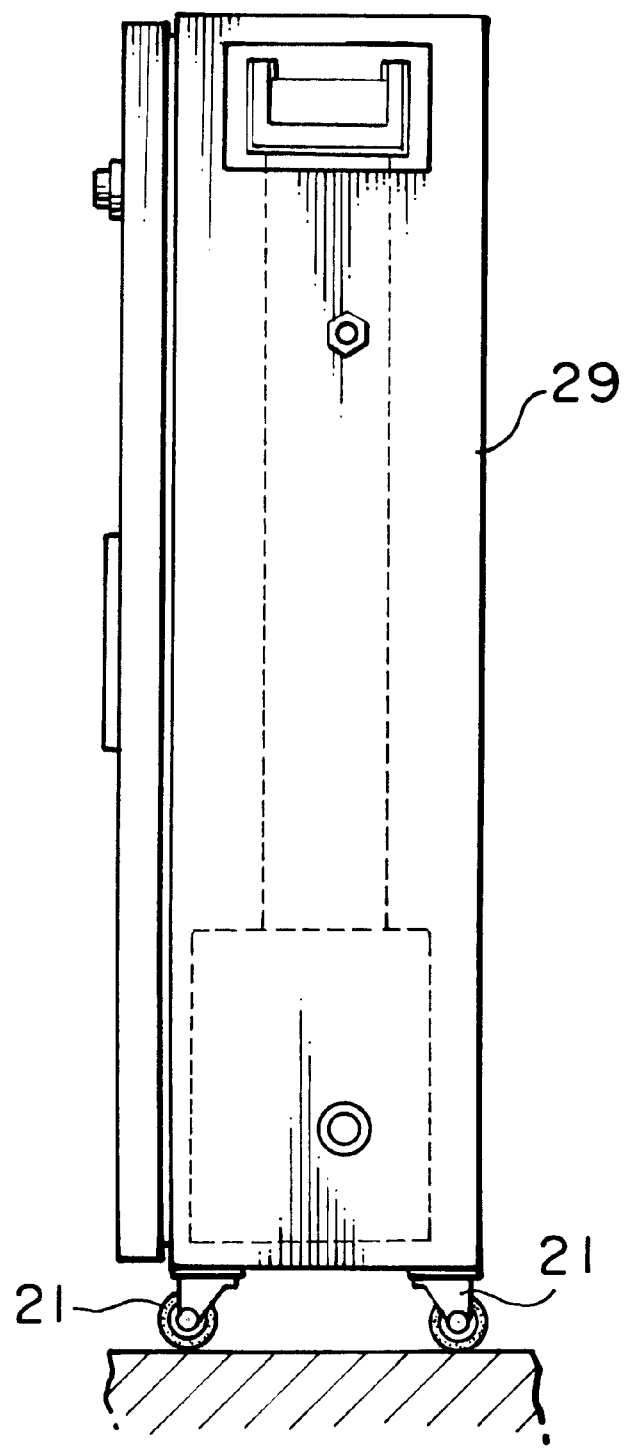
FIG. 2 is a side elevation of the indoor portion of the treatment apparatus of the present invention.
Figure 3:
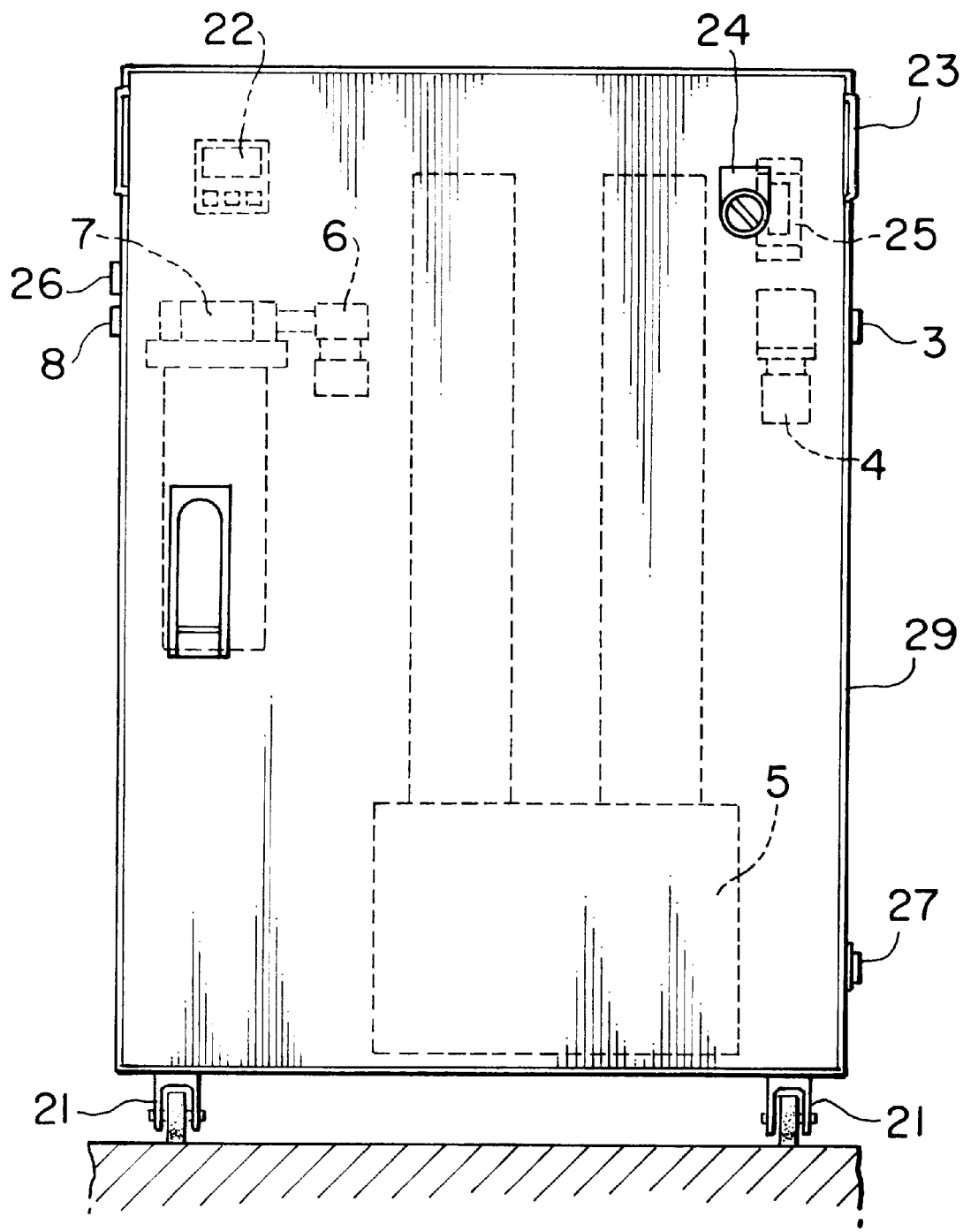
FIG. 3 is a front view of the indoor portion of the treatment apparatus of the invention.

Further, if the indoor portion of the system shown in FIG. 1 is accommodated in case 29 attached with casters 21 at the bottom plate thereof as shown in FIGS. 2 and 3, its mobility will be improved. Further, the numeral 22 denotes a temperature indicator from the cord-like temperature sensor mounted to cold wind exhaust port 20 at the leading end of tube body 10. The numeral 23 denotes a handle whereas the numeral 24 denotes a cold wind turn-off switch. Said switch may be replaced with a hand or foot switch in the designing work. The numeral 25 denotes a leakage breaker; and the numeral 26, a thermocouple; and the numeral 27, appliance coupler. Although not shown, a storage tank may be provided with an autodrain and further an air cooler may be additionally provided in case where the air compressed by the compressor will not show a natural cooling.

In operation, the compressor switched on compresses an air, from which dusts and oily substances are removed to a negligible extent, said air being further adjusted to a optimum pressure by the air pressure reducing valve and then subjected to dehumidification by heat-less drier 5. If necessary, any possible solid particles must be removed by a filter of high filtration rating. Then, a cold and hot winds are generated at vortex tube 9, said cool/hot winds being used at the time of operating a laser beam hand piece such as a laser beam surgical knife, an ultrasonic surgical knife, a massage vibrator or the like. Since said vortex tube is mounted to a laser beam hand piece by way of the metal retaining members with said mounting means being adapted to be adjusted to and secured at an optimum mounting position or angle, jetting angle, or the like by way of such mounting means, the apparatus finds wide applications not only in various medical treatments but also in industrial field such as cooling of IC chips, works, or the like.

Although the invention has so far been explained in the form of the embodiment in which the air is compressed by a compressor, it is also acceptable that compressed airs having a low dew point such as a liquefied nitrogen gas may be used to generate cold/warm winds at the vortex tube. Also, the explanation has been high-lighted on cold wind generation for medical device, the invention may be used for the massage vibrator, tools, works, or the like against which hot winds are blown. In this way, the invention covers a wide conception which may be applied to a wide range of medical, industrial and food-related areas in which cold and hot winds are used.

Thus, the present invention has, first of all, an advantage of providing a treatment apparatus which is compact, handy and easy to handle by anybody and capable of cooling, warming and drying the diseased portion to be dried.

The second advantage, in addition to the first advantage, is that the mounting angle of the vortex tube is adjusted so easily that the treatment apparatus can be directed to any diseased portion to be treated.

The third advantage, in addition to the first and second advantages, is that the mounting position of the vortex tube can be adjusted by moving the retaining metal members to and forth and rotating them with the result that the mounting position of the vortex tube and the gas jetting range can be fine tuned in addition to the advantage that the treatment apparatus can be locally directed to any diseased skin portion to be treated.

The four and fifth advantages in addition to the first through third advantages are that the dew point of the air to be compressed may be made lower such that the vortex tube can effectively generates cold or hot winds.

The sixth advantage, in addition to the fifth advantage, is that since the compressor is of an oil-free type, the maintenance work is easy while the cleanliness of the air to be used is improved, oily substances are reduced, and the solid particles are removed to a negligible extent, thus providing a highly sanitary treatment apparatus.

The seventh advantage, in addition to the first to sixth advantages, the provision of filters at the intake portion of the vortex tube makes the air used in the treatment apparatus even more sanitary and incomparable in terms of safety.

The eighth advantage, in addition to the first through seventh advantages, is that the treatment apparatus may be mounted to the laser beam hand piece such as the laser beam surgical knife, the massage vibrator, and other various works for the use of cold winds or hot winds as in the massage vibrator.

What is claimed is:

1. A medical treatment apparatus comprising:

a hand piece for medical treatment;

a vortex tube; and retaining means for adjustably retaining said vortex tube on said hand piece, and for allowing positional adjustment of said vortex tube relative to a medical treatment area, wherein said retaining means includes a first retaining member attached to said vortex tube, and a second retaining member attached to said hand piece, said first retaining member and said second retaining member being Pivotally connected to each other.

2. A medical treatment apparatus as set forth in claim 1, wherein said second retaining member is engaged with said hand piece to move back-and-forth slideably therealong and to rotate axially thereabout, said second retaining member having a fastening screw to stop said back-and-forth movement and said axial rotation of the second retaining member on the hand piece.

3. A medical treatment apparatus as set forth in claim 1, wherein said vortex tube is supplied with a liquefied gas to thereby generate cold and hot gas streams therewithin.

4. A medical treatment apparatus as set forth in claim 1, wherein said vortex tube is supplied with high pressure compressed and dehumidified air to thereby generate cold and hot gas streams therewithin.

5. A medical treatment apparatus comprising:

a hand piece for medical treatment;

a vortex tube; and retaining means for adjustably retaining said vortex tube on said hand piece, and for allowing positional adjustment of said vortex tube relative to a medical treatment area, wherein said apparatus further including an oil-free scroll type compressor; an air filter assembly; a heat-less drier; an electromagnetic valve; and a filter; and wherein said oil-free scroll type compressor, said air filter assembly, said heat-less drier, said electromagnetic valve and said filter are connected in series to communicate with said vortex tube.

6. A medical treatment apparatus as set forth in claim 1, wherein said hand piece includes a laser beam treatment utensil which includes at least one work piece selected from the group consisting of a laser beam surgical knife, an ultrasonic surgical knife, and a massage vibrator.

\* \* \* \* \*